(12) United States Patent
Grzeda et al.

(10) Patent No.: US 9,008,279 B2
(45) Date of Patent: Apr. 14, 2015

(54) C-ARM ROTATION ENCODING METHODS AND APPARATUS

(75) Inventors: Victor Grzeda, Sault Ste. Marie (CA); Gabor Fichtinger, Kingston (CA)

(73) Assignee: Queen's University at Kingston, Kingston (CA)

( * ) Notice: Subject to any disclaimer, the term of this patent is extended or adjusted under 35 U.S.C. 154(b) by 831 days.

(21) Appl. No.: 13/166,267

(22) Filed: Jun. 22, 2011

(65) Prior Publication Data

US 2011/0311030 A1 Dec. 22, 2011

Related U.S. Application Data

(60) Provisional application No. 61/357,459, filed on Jun. 22, 2010.

(51) Int. Cl.
*H05G 1/26* (2006.01)
*A61B 6/00* (2006.01)

(52) U.S. Cl.
CPC ............ *A61B 6/4441* (2013.01); *A61B 6/487* (2013.01); *A61B 6/5205* (2013.01); *A61B 6/527* (2013.01); *A61B 6/547* (2013.01)

(58) Field of Classification Search
CPC .... G03B 42/047; A61B 6/4441; A61B 19/54; A61B 6/12; A61B 6/583; A61B 19/0082
USPC .......................................... 378/62, 162, 207
See application file for complete search history.

(56) References Cited

U.S. PATENT DOCUMENTS

| | | | | |
|---|---|---|---|---|
| 6,461,040 B1* | 10/2002 | Mattson et al. | ............... | 378/205 |
| 2005/0049486 A1* | 3/2005 | Urquhart et al. | ............... | 600/429 |
| 2006/0025677 A1* | 2/2006 | Verard et al. | ................... | 600/423 |
| 2008/0262338 A1* | 10/2008 | Paitel et al. | ................... | 600/409 |

OTHER PUBLICATIONS

Barshan B, et al., Inertial navigation system for mobile robots. IEEE Trans Robotics Automation 11(2):328-245 (1995).
Batista J, et al., Pose view stability analysis for camera look angles computation. In: Proceeding of the 13th International Conference on Pattern Recognition (ICPR), pp. 171-175 (1996).
Jain A, et al., Intra-operative 3D guidance in prostate brachytherapy using a non-isocentric C-arm. Medical Image Computing and Computer-Assisted Intervention 10(Pt 2):9-17 (2007).
Jain A, et al., C-arm tracking and reconstruction without an external tracker. Medical Image Computing and Computer-Assisted Intervention 9(Pt 1):494-502 (2006).
Jain A, et al., FTRAC—A robust fluoroscope tracking fiducial. Medical Physics 32(10):3185-3198 (2006).

(Continued)

*Primary Examiner* — Irakli Kiknadze
(74) *Attorney, Agent, or Firm* — Stephen J. Scribner

(57) ABSTRACT

This invention provides a method for estimating C-ARM fluoroscope rotation pose, and related programmed media and kits. In one embodiment the method includes measuring an angle of the C-arm using an accelerometer affixed to the C-arm, wherein the accelerometer is not moving during the measurement. The method includes generating angle correction equations based on differences between C-arm poses and corresponding accelerometer angles, and optionally generating structural compensation equations to compensate for structural flexion or deformation of the C-arm.

16 Claims, 11 Drawing Sheets

Primary Angle Rotation

Secondary Angle Rotation

(56) References Cited

OTHER PUBLICATIONS

Nikbakht S, et al., Evaluation of solid-state accelerometer for positioning of vehicle. IEEE International Conference on Industrial Technology (ICIT), pp. 729-733 (2005).

Thong YK, et al., Numerical double integration of acceleration measurement in noise. Measurement 36:73-92 (2004).

Gorges S, et al., Model of a Vascular C-Arm for 3D Augmented Fluoroscopy in Interventional Radiology, MICCAI 2005, Lecture Notes in Computer Science vol. 3750, pp. 214-222, Springer (2005).

Lee J, et al., Prostate brachytherapy seed reconstruction with Gaussian blurring and optimal coverage cost. IEEE Trans Med Imaging,28(12):1955-68 (2009).

Birkfellner W, et al., Tracking Devices, In: Image-Guided Interventions: Technology Applications, Chapter 2, pp. 23-44 (2008), Peters T and Cleary K (eds.), Springer Science.

Tan CW et. al., Design of accelerometer-based inertial navigation system. IEEE Transactions on Instrumentation and Measurement 54(6): 2520-2530 (2005).

Yao J, et al., A C-arm fluoroscopy-guided progressive cut refinement strategy using a surgical robot. Computer Aided Surgery 5(6):373-90 (2000).

Zhang NF, Calculation of the uncertainty of the mean of autocorrelated measurements. Metrologia 43: S276-S281 (2006).

\* cited by examiner

| ROTATION DEG° | PRIMARY ANGLE | | | | | | | | | | | | |
|---|---|---|---|---|---|---|---|---|---|---|---|---|---|
| SECONDARY ANGLE | 30 | 25 | 20 | 15 | 10 | 5 | 0 | -5 | -10 | -15 | -20 | -25 | -30 |
| 30 | | | | | | | -1.29 / 29.99 | | | | | | |
| 25 | | 24.07 / 27.68 | | | | | -1.19 / 24.92 | | | | | -25.94 / 26.86 | |
| 20 | | | 18.91 / 21.38 | | | | -1.12 / 20.05 | | | | -20.86 / 21.19 | | |
| 15 | | | | 14.08 / 15.58 | | | -0.66 / 15.09 | | | -15.67 / 15.54 | | | |
| 10 | | | | | 9.14 / 10.15 | | -0.51 / 10.05 | | -10.70 / 10.68 | | | | |
| 5 | | | | | | 4.60 / 4.98 | -0.38 / 5.18 | -5.64 / 5.53 | | | | | |
| 0 (PA / SA) | 29.75 / -0.66 | 24.59 / -0.72 | 19.77 / -0.66 | 14.77 / -0.69 | 9.58 / -0.65 | 4.68 / -0.62 | -0.23 / 0.12 | -5.13 / 0.44 | -10.14 / 0.44 | -14.88 / 0.00 | -20.06 / -0.31 | -25.09 / -0.77 | -29.95 / -1.22 |
| -5 | | | | | | 4.96 / -4.95 | 0.02 / -4.71 | -5.07 / -4.28 | | | | | |
| -10 | | | | | 10.05 / -9.66 | | 0.26 / -9.68 | | -9.85 / -9.59 | | | | |
| -15 | | | | 15.32 / -15.43 | | | 0.55 / -14.62 | | | -14.90 / -15.29 | | | |
| -20 | | | 20.27 / -21.28 | | | | 0.46 / -19.68 | | | | -19.99 / -21.75 | | |
| -25 | | 25.02 / -27.78 | | | | | 0.38 / -24.85 | | | | | -24.71 / -28.40 | |
| -30 | | | | | | | 0.43 / -30.23 | | | | | | |

Figure 9

| ROTATIONS | PRIMARY ANGLE | | | | | | | | | | | | | | | |
|---|---|---|---|---|---|---|---|---|---|---|---|---|---|---|---|---|
| DEG° | 26 | 22 | 18 | 14 | 10 | 6 | 2 | 0 | -2 | -6 | -10 | -14 | -18 | -22 | -26 | |
| 26 | | | | | | | | 0.04 / 26.26 | | | | | | | | |
| 22 | | 22.34 / 21.45 | | | | | | 0.11 / 22.20 | | | | | -21.74 / 21.55 | | | |
| 18 | | | 18.34 / 17.74 | | | | | 0.17 / 18.39 | | | | -17.99 / 17.91 | | | | |
| 14 | | | | 14.47 / 13.91 | | | | 0.30 / 14.22 | | | -13.89 / 13.99 | | | | | |
| 10 | | | | | 10.35 / 9.86 | | | 0.04 / 10.36 | | -9.78 / 10.24 | | | | | | |
| 6 | | | | | | 6.25 / 5.61 | | 0.14 / 6.23 | -6.16 / 6.37 | | | | | | | |
| 2 | | | | | | | 2.05 / 1.68 | 0.07 / 2.05 | -2.06 / 2.21 | | | | | | | |
| 0 | 26.04 / -0.30 | 21.87 / -0.30 | 18.04 / -0.43 | 14.02 / -0.68 | 10.12 / -0.56 | 6.02 / -0.77 | 2.31 / -0.61 | 0.29 / 0.20 | -1.69 / 0.25 | -5.87 / 0.42 | -9.64 / 0.27 | -13.69 / 0.22 | -17.17 / 0.04 | -21.62 / 0.02 | -25.70 / 0.07 | PA / SA |
| -2 | | | | | | | 2.08 / -1.91 | 0.12 / -1.40 | -2.04 / -1.84 | | | | | | | |
| -6 | | | | | | 5.82 / -5.98 | | 0.15 / -5.72 | -6.08 / -5.71 | | | | | | | |
| -10 | | | | | 9.94 / -9.94 | | | 0.06 / -9.49 | | -9.79 / -9.70 | | | | | | |
| -14 | | | | 13.66 / -13.71 | | | | 0.17 / -13.87 | | | -14.03 / -13.56 | | | | | |
| -18 | | | 17.82 / -17.38 | | | | | 0.15 / -18.07 | | | | -18.22 / -17.33 | | | | |
| -22 | | 21.67 / -21.36 | | | | | | 0.10 / -21.88 | | | | | -22.07 / -21.20 | | | |
| -26 | | | | | | | | 0.02 / -25.99 | | | | | | | | |

Figure 11

| ROTATIONS | | PRIMARY ANGLE | | | | | | |
|---|---|---|---|---|---|---|---|---|
| | DEG° | 12 | 8 | 4 | 0 | -4 | -8 | -12 |
| SECONDARY ANGLE | 12 | | | | 0.12<br>12.18 | | | -11.72<br>12.05 |
| | 8 | 12.45<br>8.09 | | | 0.11<br>8.20 | | | -11.78<br>8.22 |
| | 4 | | 8.38<br>4.10 | | 0.17<br>4.11 | | -7.72<br>4.06 | |
| | 0 | | | 4.23<br>-0.14 | 0.16<br>-0.02 | -3.83<br>0.14 | | PA<br>SA |
| | -4 | | 8.10<br>-4.17 | | 0.13<br>-4.10 | | -7.55<br>-4.19 | |
| | -8 | 11.76<br>-8.32 | | | 0.45<br>-8.09 | | | -11.54<br>-7.99 |
| | -12 | 11.81<br>-12.36 | | | 0.39<br>-12.55 | | | |

C-ARM ROTATION ENCODING METHODS AND APPARATUS

RELATED APPLICATION

This application claims the benefit of the filing date of U.S. Provisional Patent Application No. 61/357,459, filed on 22 Jun. 2010, the contents of which are incorporated herein by reference in their entirety.

FIELD

This invention is in the field of C-arm fluoroscopy. In particular, this invention is provides methods and apparatus for accurately determining C-arm rotational pose.

BACKGROUND

Fluoroscopic C-arms are an important tool in computer-assisted interventions. For example, a fluoroscopic C-arm may be used in computer-assisted applications to reconstruct anatomical structures and objects in 3D from their 2D X-ray images. Reconstruction requires the relative pose of the 2D projection images, a problem commonly known as C-arm pose tracking.

Accurate, practical, and affordable C-arm pose tracking is a major technical challenge. There are motorized C-arm devices that provide rotational pose information, but they are rather expensive and susceptible to pose errors due to wheel motion, sagging, and deformation of the device. Conventional manual C-arms are supplanted with some tracking method to recover the C-arm pose. Tracking may take two forms, external or X-ray image-based. In external tracking, an object called a dynamic reference body (DRB) is attached to the C-arm, while the pose of the DRB is sensed by optical cameras or electromagnetically [7]. External tracking produces full six degrees of freedom (DOF) pose of the C-arm and is resistant to wheel motion, sagging and deformation of the C-arm. Optical tracking is usually more accurate, but requires line of sight. Electromagnetic tracking does not demand line of sight, but is susceptible to field distortions typically caused by the presence of metallic objects or even the earth's magnetic field. A further shortcoming is that prior to using the system the DRB needs to be pre-calibrated to the C-arm image. In all, external tracking tends to add significant cost and complexity to the system. In image-based tracking, a radio-opaque object of known geometry (commonly referred as fiducial) is placed in the field of imaging [5, 11]. If the fiducial has sufficient specificity, then the full 6 DOF pose of the C-arm image can be computed relative to the fiducial. While image-based tracking is inexpensive and potentially accurate, the fiducial occupies valuable real estate in the image.

An alternative tracking method is the use of accelerometers to recover the pose. The initial theory postulated the use of accelerometers as a positional tracker, by performing a double integration of the acceleration information to retrieve positional information. Several previously published papers have used accelerometers in position tracking mainly for robotic applications [1, 8, 9]. However, applying similar methodologies to recover the C-arm pose proved problematic. Setting aside the inherent issues with accelerometers, such as noise, bias, and drift [10, 12], the mechanical properties of the C-arm did not allow for the accelerometer positional tracking methods to perform to an acceptable level of accuracy. The main issue stems from the C-arm rotations. The accelerometer senses motion and gravity forces. This means that when the C-arm rotates along its primary or secondary axis, the accelerometer will output readings caused by both forces. This makes it extremely difficult to discern the true motion required for pose tracking. If the accelerometer is coupled with a gyroscope, it will give orientation, which helps isolate the effects of static gravity. Knowing the static gravity, it can be subtracted from the accelerometer readings, thereby giving true motion acceleration at each time interval. This is a very complex and potentially costly strategy. Thus there is a need for a new technique to recover the C-arm fluoroscope rotation pose.

SUMMARY

Provided herein is a method for estimating C-ARM fluoroscope rotation pose, comprising measuring an angle of the C-arm using an accelerometer affixed to the C-arm, wherein the accelerometer is not moving during the measurement.

In one embodiment the method may comprise: providing a means for determining ground truth of a fluoroscopy image space; acquiring a first set of fluoroscopy images at a plurality of C-arm poses and obtaining accelerometer angles for primary angles (PAs) and secondary angles (SAs) of each C-arm pose; calculating an actual C-arm pose for each image using the ground truth;determining differences between actual C-arm poses and corresponding accelerometer angles; generating angle correction equations by applying a best fit model to the differences; and using the angle correction equations to determine C-arm fluoroscopy rotation pose of subsequent C-arm fluoroscopy images.

In another embodiment the method may comprise generating structural compensation equations (SCEs) by: processing images with diagonal combinations of PA and SA; computing and zeroing errors for the PA and SA separately; and applying line fitting to differences between actual C-arm poses and corresponding accelerometer angles; wherein the method includes using angle correction equations and structural compensation equations to determine C-arm fluoroscopy rotation pose of subsequent C-arm fluoroscopy images. The method may comprise determining a threshold value $\tau$; and using $\tau$ to control when to activate the structural compensation equations depending on angle values for PA and SA.

The method may comprise using a fiducial to determine ground truth of the fluoroscopy image space, or using a tracker to determine ground truth of the fluoroscopy image space.

Applying a best fit model to the differences may comprise applying a linear regression model to the differences, or applying a polynomial regression model to the differences.

The method may comprise acquiring the first set of fluoroscopy images at a range of poses corresponding to a range of primary and secondary angles of the fluoroscope during use on a patient.

Also provided herein is programmed media for use with a computer and a fluoroscope including an accelerometer, the programmed media comprising: a computer program stored on storage media compatible with the computer, the computer program containing instructions to direct the computer to perform one or more of: input ground truth data of a fluoroscopy image space; acquire a first set of fluoroscopy images at a plurality of C-arm poses and obtain accelerometer angles for primary and secondary angles of each C-arm pose; calculate an actual C-arm pose for each image using the ground truth; determine differences between actual C-arm poses and corresponding accelerometer angles; generate angle correction equations by applying a best fit model to the differences; use the angle correction equations to determine C-arm fluoroscopy rotation pose of subsequent C-arm fluoroscopy images; and output rotation pose data of the subsequent C-arm fluoroscopy images.

In one embodiment the computer program may direct the computer to: process images with diagonal combinations of PA and SA; compute and zero errors for the PA and SA separately; apply line fitting to differences between actual C-arm poses and corresponding accelerometer angles to generate structural compensation equations; and use angle correction equations and structural compensation equations to determine C-arm fluoroscopy rotation pose of subsequent C-arm fluoroscopy images.

In another embodiment the computer program may direct the computer to: determine a threshold value τ; and use τ to control when to activate the structural compensation equations depending on angle values for PA and SA.

Also provided herein is a kit, comprising: an accelerometer; and the programmed media described above. The kit may comprise hardware for interfacing the accelerometer with a C-arm fluoroscope and/or with a computer. The kit may comprise means for determining ground truth of the fluoroscope. In one embodiment the means for determining ground truth of the fluoroscope comprises a tracker or a fiducial.

BRIEF DESCRIPTION OF THE DRAWINGS

For a better understanding of the invention, and to show more clearly how it may be carried into effect, embodiments will be described, by way of example, with reference to the accompanying drawings, wherein:

FIG. 9 is a chart wherein inner cells show actual C-arm pose angles: PA (above), SA (below); and C-arm pose positions using ACEs accelerometer readings are shown in the outside border.

FIG. 11 is a chart similar to that of FIG. 9 showing results obtained using ACEs and structural compensation equations (SCEs).

DETAILED DESCRIPTION OF EMBODIMENTS

Figure 1:
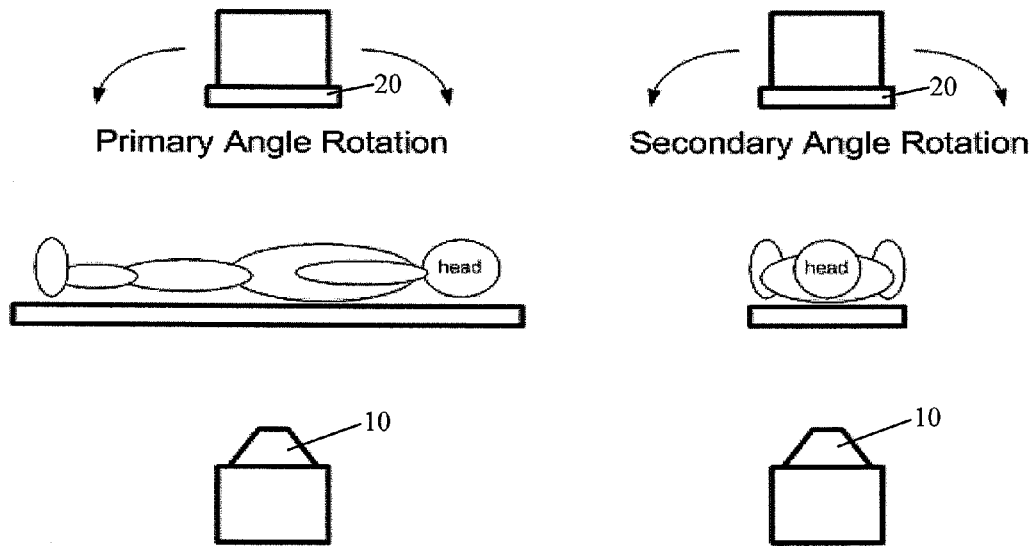
FIG. 1 is a diagrammatic representation of C-arm rotational axes relative to the placement of a patient.

A typical C-arm flouroscopy system, shown in FIG. 1, includes an x-ray source 10 and an image intensifier 20, at opposite ends of the C-arm (not shown). The image intensifier may be a digital flat panel acquisition unit. Magnification depends on the source to object distance (SOD), source to intensifier distance (SID), and the intensifier size (IS). A biplane system has two C-arm units rotating around a common isocenter, wherein images are acquired on the two systems nearly simultaneously (e.g., within 10-15 ms).

As shown in FIG. 1, orientation of the C-arm with respect to the patient is defined by two angles. The primary angle (PA) represents rotation of the C-arm along an arc from the patient's head to feet. The secondary angle (SA) represents rotation of the C-arm along an arc from patient's left to right sides. The primary and secondary angles define the geometric orientation of the imaging system with respect to the patient. Zero degree primary and secondary angles correspond to an anterior-posterior projection.

Described herein is a method and apparatus for estimating or determining C-arm fluoroscope rotation pose by using the angle-sensing capabilities of an accelerometer. A clinical application for the embodiments described herein is intraoperative implant reconstruction in prostate cancer brachytherapy [3]; however, the embodiments are not limited thereto, and they may be applied in any imaging application where accurate estimation of the C-arm pose is required. In the example of intra-operative implant reconstruction in prostate cancer brachytherapy, the C-arm is operated in a step-and-shoot mode within a limited set of rotational angles. This limitation is approximately a 40-degree cone about the canonical vertical pose of the C-arm, where both rotational axes of the C-arm move between ±20 degrees. Factors that create this constraint are potential collision with patient, operating room table, and other standard instrumentation used in the procedure. For successful reconstruction of the brachytherapy implants the C-arm pose needs to be recovered with an accuracy of about 1.0 degree [3, 7].

Methods described herein include recovering the C-arm rotational pose (i.e., tilt angle) using an angle-sensing device, such as an accelerometer. For example, affixing an accelerometer to a C-arm allows the C-arm pose to be estimated at any position (i.e., angle) through its rotational range. In embodiments described herein, static gravitational angle of the C-arm is measured, wherein the C-arm and hence the accelerometer is not moving during measurements. This effectively eliminates other forces such that gravity is the only relevant force acting on the accelerometer. By measuring an offset between accelerometer angle readings and the image pose angle, an angle correction equation (ACE) may be derived to properly track the C-arm rotational pose. In various embodiments derivation of the ACE may be carried out using by fitting linear or polynomial models to the C-arm angle data and accelerometer angle data. In one embodiment, the method includes one or more refinement steps in deriving the ACE wherein different models (linear, 2-, 3-, 4-order polynomial, etc.) are fit to the data and the best fitting model used for subsequent steps. Methods described herein track the C-arm pose with a clinically relevant accuracy of less than 1.0 degree.

Accelerometer angle encoding as described herein includes a one-time calibration step to relate the raw accelerometer angle to the C-arm pose. In one embodiment, the linear workflow includes the following steps: (1) Mount an accelerometer on the C-arm; (2) Place a ground truth (e.g., a C-arm tracking fiducial) in the field of view; (3) Acquire test images while logging the initial rotation pose from the accelerometer; (4) Compute reference poses using the fiducial; (5) Compute the offset for both primary and secondary C-arm angles; and (6) Confirm the accuracy of calibration on a subset of independent measurements not used in the calibration computations. One such uncertainty is the effect of wheel motion.

A feature of the instant methods is the ability to overcome possible inaccuracies that may be introduced by the C-arm apparatus. For example, mobile C-arms have wheels and use wheel locks to secure the apparatus in place. During rotational movement the C-arm may experience rocking and swinging motions that affect the pose of the image. However, since an accelerometer is used in the instant embodiments, real-time analysis of acceleration readings can detect acceleration spikes. These spikes indicate rapid motion changes (e.g., rocking, swaying) of the C-arm. By continuously monitoring for the spike to subside (i.e., steady state) a "go-ahead" signal can be flagged to indicate when images can be captured, thereby avoiding added error to the image pose.

Embodiments described herein use parameters that are determined from the C-arm and accelerometer combination. These include a set of angle correction equations (ACEs) that account for the initial offset between the raw accelerometer angle readings and the C-arm pose. Generating the ACEs involves analyzing differences between the initial accelerometer angle reading and ground-truth pose angle. Embodiments may also include a set of structural compensation equations (SCEs) that account for deformation of the C-arm during different rotational poses. Following a one-time calibration of the C-arm to determine the ACEs and SCEs, these equations remain valid for continued use of the C-arm given that the accelerometer remains fixed on the gantry.

Methods of acquiring a series of test images and modeling the structural deformation of the C-arm was described by Gorges et al. [13]; however, that work involved modeling the deformation as changes to the intrinsic/extrinsic parameters of the C-arm, and using cost functions to optimize the parameters to account for the deformations.

Also described herein is programmed media for use with a computer and a C-arm fluoroscope including an accelerometer, the programmed media comprising a computer program stored on storage media compatible with the computer, the computer program containing instructions to direct the computer to perform one or more of the steps for determining C-arm pose as described herein. The steps may include generating the ACEs and/or the SCEs.

Also described herein is a kit that allows the methods described herein to be applied to any C-arm fluoroscope. The kit includes an accelerometer, hardware for interfacing (wired or wirelessly) the accelerometer with the fluoroscope and a computer, software for collecting and analyzing data using the computer, and instructions for installation and use. The kit may also include hardware used for determining ground truth of the fluoroscope, such as, for example, a tracker or a fiducial.

The contents of all references, pending patent applications, and published patents cited throughout this application are hereby expressly incorporated herein by reference.

Embodiments are further described by way of the following non-limiting examples:

EXAMPLE 1

Accelerometer

An accelerometer is small and low cost, and has low power requirements, which allow it to be a self-contained sensing system. Since accelerometers can accurately measure the force of gravity and the accelerometer has known geometric properties, they may be reconfigured into tilt (angle) sensors. While accelerometers may be custom made for a desired application, many general purpose packages are widely available ranging from 1, 2, and 3 DOF sensors. The most common use of accelerometers are in inertial measurements for determining orientation (roll, pitch, and yaw), which we also use to find the C-arm pose. The approach described herein includes measuring the influence of gravity at each axis. In a stable state with no motion force, each axis will measure a component of the overall gravity force of 1 g, shown in Equation 1. Knowing this property, calculating the desired angles is a matter of taking the appropriate ratios of the accelerometer values from each axis [2]. Equation 2 gives an example, where $\alpha$ is the angle along x-axis and /$\beta$ is the angle along the y-axis.

$$\sqrt{A_x^2 + A_y^2 + A_z^2} = 1 \text{ g} \tag{1}$$

$$\alpha = \tan^{-1}\left(\frac{A_x}{\sqrt{A_y^2 + A_z^2}}\right) \tag{2}$$

$$\beta = \tan^{-1}\left(\frac{A_y}{\sqrt{A_x^2 + A_z^2}}\right)$$

In an experimental prototype a Sparkfun™ Electronics WiTilt v3 packaged device was used. This device is intended for general purpose applications containing a Freescale MMA7260Q triple axis accelerometer with a class 1 Bluetooth® communication link. The small package allows for placing the accelerometer on the detector or source without interfering with normal use of the C-arm and the wireless communication does not intrude upon the operating room. For convenience, the accelerometer axes were aligned approximately with the rotational axes of the C-arm.

Calibration

Figure 2:
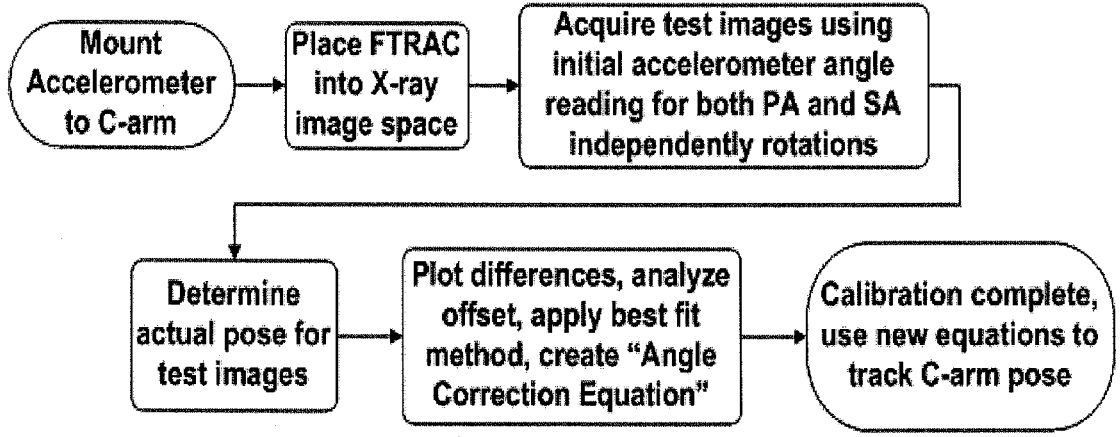
FIG. 2 is a block diagram showing steps for C-arm pose tracking with an accelerometer according to one embodiment.

Once the accelerometer is in place on the C-arm, axes of the accelerometer are calibrated to the rotation axes of the C-arm. The calibration requires an independent pose tracking ground truth, provided by either an external tracker or by tracking a fiducial. For example, the fluoroscope tracking fiducial (FTRAC) developed by Jain et al. [3] may be used. Then the accelerometer pose estimate can be compared directly to this ground truth. FIG. 2 shows a flowchart of C-arm pose tracking using the accelerometer angle.

One of the most important aspects is the initial mounting of the accelerometer to the C-arm. As mentioned earlier, the small device packaging makes it ideal and convenient to place on the C-arm detector or source. By properly securing and calibrating the device, subsequent uses will continue to be valid with the computed calibration offset. The C-arm is calibrated and the intrinsic and extrinsic parameters saved. Next, several test images are taken using the initial reading of the accelerometer. These readings are used to determine the offset between the C-arm pose and accelerometer. The test angles should ensure that the angles have enough separation and a sufficiently wide range to account for possible variations of the primary and secondary angles when the C-arm is in motion. The final step is to calculate the actual C-arm pose of these test images using the ground truth tracker and analyze the differences between the ground truth and the initial angle measurements. Then a best-fit method is applied to the PA and SA errors, to obtain the quantifiable offset termed Angle Correction Equations (ACEs), which completes calibration of the accelerometer to the C-arm.

C-arm Analogue

Figure 3A:
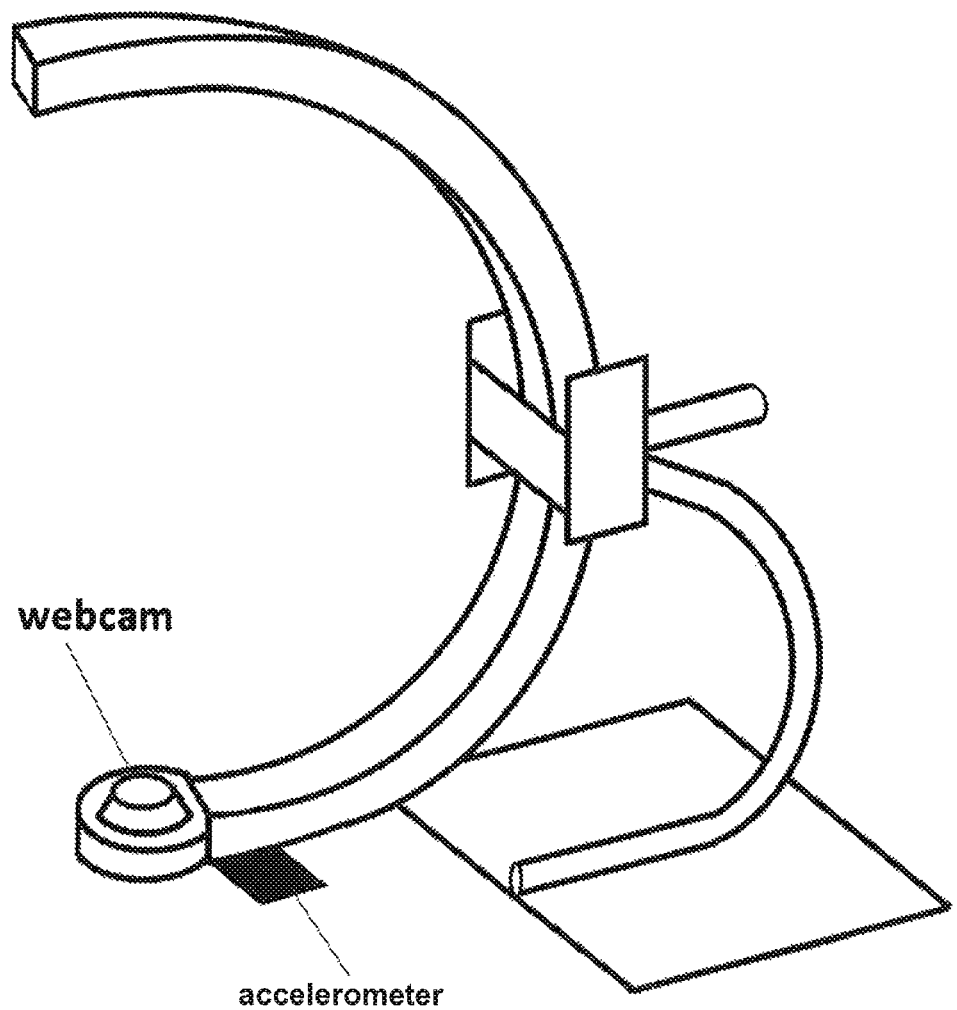
FIG. 3(a) is a diagram of a C-arm analogue equipped with a webcam, wherein the C-arm is positioned upside-down to better show the construction of the C-arm.
Figure 3B:
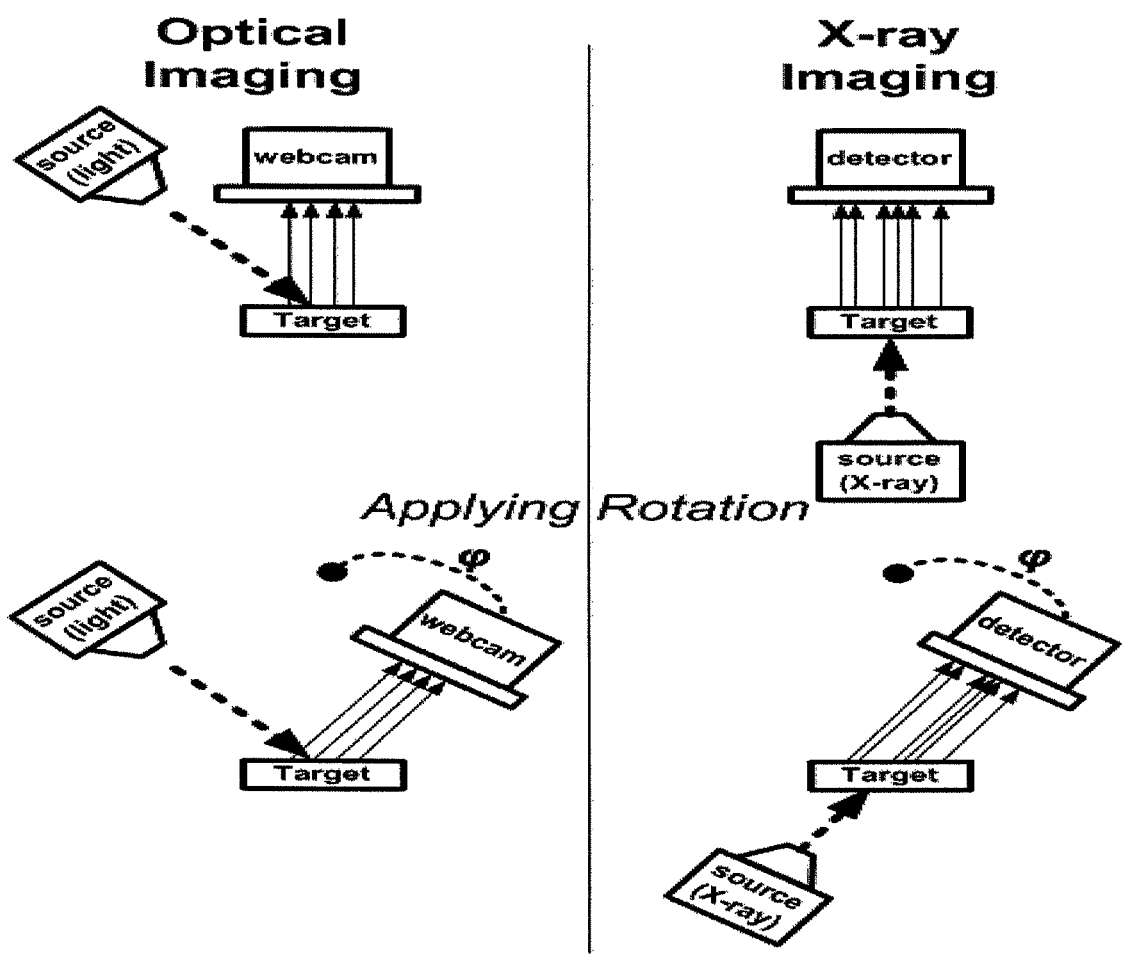
FIG. 3(b) is a diagram showing how 2-D images are created in X-ray and optical imaging modalities, and their similarities during rotations.

To evaluate the concept on an actual C-arm would involve harmful ionizing radiation. To reduce the laboratory turnaround time and eliminate radiation exposure, a radiation-free downscaled model of a C-arm was constructed. The model shown in FIG. 3(a) mimics the mechanical rotations of a full size clinical C-arm. To mimic X-ray imaging, a Microsoft LifeCam VX-3000 webcam was attached to the top end of the C-arm analogue. Just as in X-ray imaging, optical imaging creates 2D images even though the principle of the imaging modalities is different. Creating a 2D image involves using a source and apparatus to capture the image, shown in FIG. 3(b). In X-ray imaging, photons are expelled from the point source. The photons travel in a straight line, through the target and hit the detector to create a 2D shadow of the target. Optical imaging uses the same geometrical principle, but the photons move in the opposite direction: visible light from the target travels in a straight line towards the camera.

Figure 4:
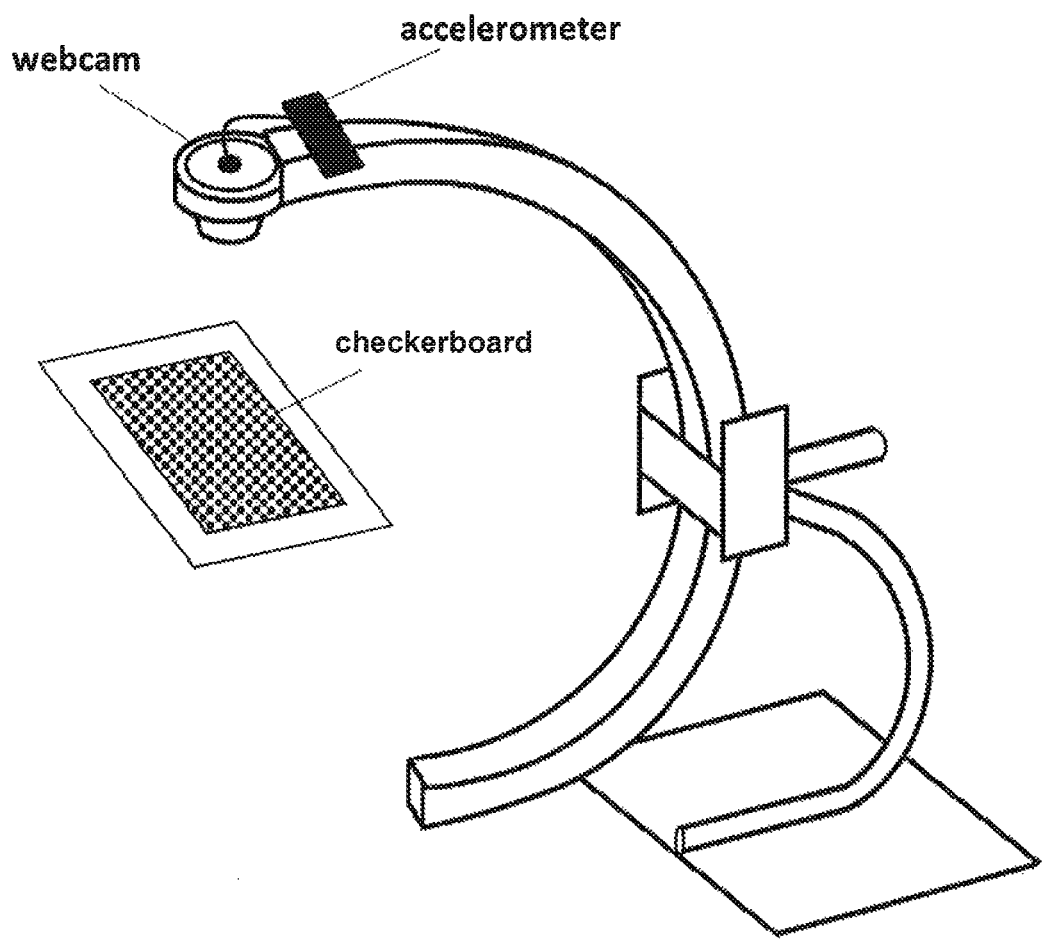
FIG. 4 is a diagram showing a setup for the C-arm analogue of FIG. 3(a), with checker board for calibration and ground truth for pose tracking.

The setup is shown in FIG. 4, with a checkerboard placed on top of a case stand that was near the center point of the C-arm. The webcam was pre-calibrated to the accelerometer using the checker board. A MATLAB program read the acceleration data and computed the angle by taking 50 sets of filtered samples, and averaging each before being displayed on-screen. For rotational pose calibration, 20 primary angles (PA) and 20 secondary angles (SA) were taken at random angles to compute the intrinsic and extrinsic camera parameters. Camera calibration was achieved by a MATLAB toolbox [3].

Experiments and Results

First, the offset between the accelerometer angle and the webcam C-arm pose was determined. The samples angle set for the test images were at [0°±4°±8°±12°±16°±20°] for PA and SA separately, giving an evenly spaced wide range of angles for experimentation. To calculate the ground truth angles the intrinsic parameter, computed in the camera calibration step, was used to compute the extrinsic parameters for each test image. Within the extrinsic parameters is a rotational matrix that corresponds to the transform between the 2D-image to its 3D-orientation. When this matrix is broken down into individual angular components, the components can be interpreted as the actual angles for the PA and SA [2], respectively. The calculated offset is shown in Table 1, obtained by subtracting the accelerometer angle reading from the webcam C-arm pose.

TABLE 1

Calibration - differences between accelerometer angles and webcam angles

| Accelerometer Readings | Primary Angle (PA) | | Secondary Angle (SA) | |
| --- | --- | --- | --- | --- |
| | Webcam Angles | Differences | Webcam Angles | Differences |
| −20 | −18.91 | 1.09 | −21.73 | −1.73 |
| −16 | −14.56 | 1.44 | −17.33 | −1.33 |
| −12 | −10.49 | 1.51 | −13.46 | −1.46 |
| −8 | −6.63 | 1.37 | −9.35 | −1.35 |
| −4 | −2.36 | 1.64 | −5.61 | −1.61 |
| 0 | 1.73 | 1.73 | 1.39 | 1.39 |
| 4 | 5.88 | 1.88 | 2.59 | −1.41 |

TABLE 1-continued

Calibration - differences between accelerometer angles and webcam angles

| Accelerometer Readings | Primary Angle (PA) | | Secondary Angle (SA) | |
| --- | --- | --- | --- | --- |
| | Webcam Angles | Differences | Webcam Angles | Differences |
| 8 | 9.85 | 1.85 | 6.69 | −1.31 |
| 12 | 14.03 | 2.03 | 10.89 | −1.11 |
| 16 | 18.22 | 2.22 | 14.78 | −1.22 |
| 20 | 22.33 | 2.33 | 18.73 | −1.27 |

Figure 5A:
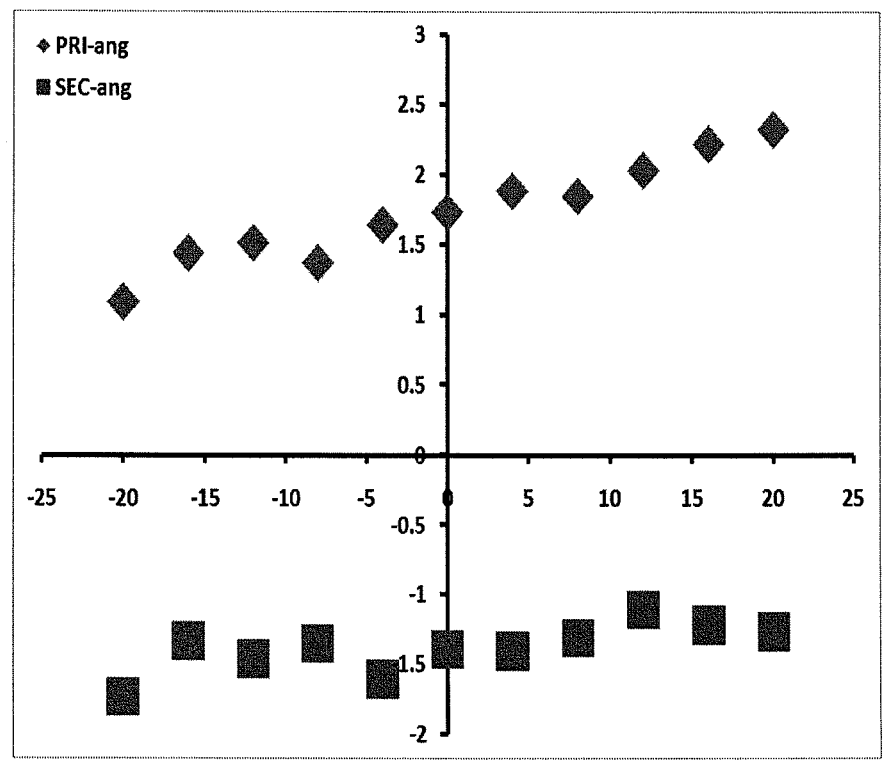
FIG. 5(a) is a graphical visualization of the difference between accelerometer angles and webcam angles for the setup of FIG. 4.
Figure 5B:
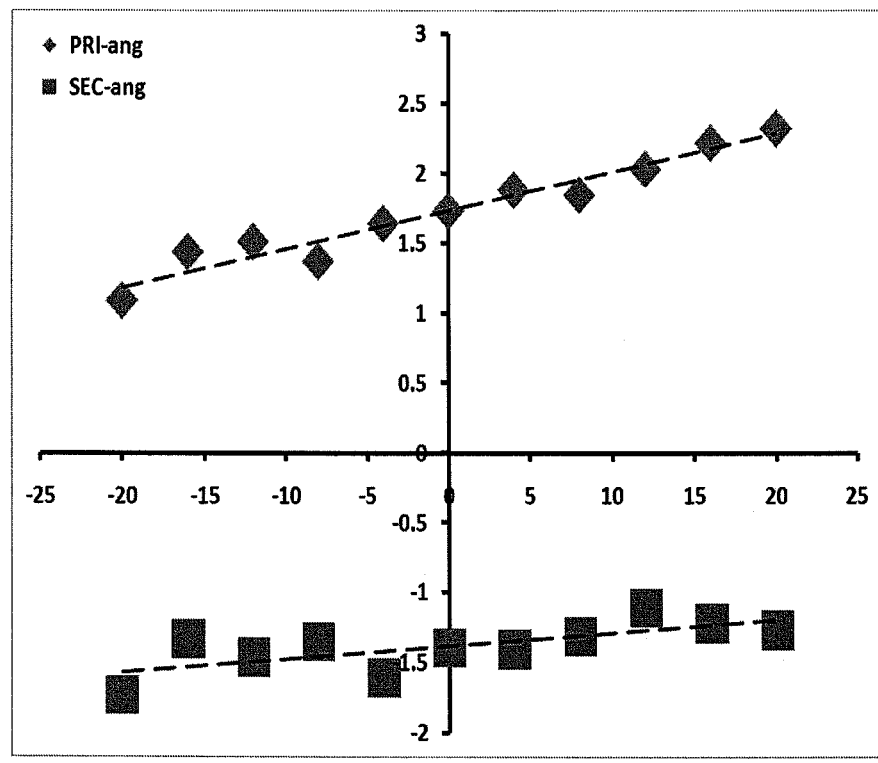
FIG. 5(b) shows a linear best fit over the data points used to create angle correction equations (ACEs).

To better interpret the error shown in Table 1, the plots shown in FIG. 5 (a) were created. The data points were fitted with least square optimization to straight lines shown in FIG. 5 (b). The fitting resulted in a quantifiable offset in the form of the ACE. The ACEs for the PA and SA are expressed in Equations (3) and (4), respectively.

$$\text{Let } x \text{ represent initial } PA \text{ then the new } PA' = 1.027.x + 1.734 \quad (3)$$

$$\text{Let } z \text{ represent initial } SA \text{ then the new } SA' = 1.009.z + 1.381 \quad (4)$$

The accuracy of ACE in tracking the webcam C-arm pose was characterized. The principle behind the above equations is a conversion process from the initial accelerometer angle reading to a corrected accelerometer angle output. To judge whether ACE was a viable method for tracking, the angular settings for PA and SA test images were changed to [0°±2°±6°±10°±14°±18°], in order to avoid using the same angles as we used for creating the ACE. Table 2 shows the differences between the accelerometer angle readings and the webcam pose.

TABLE 2

Validation of the Correction Equation (ACE)

| Accelerometer Readings | Primary Angle (PA) | | Secondary Angle (SA) | |
| --- | --- | --- | --- | --- |
| | Webcam Angles | Differences | Webcam Angles | Differences |
| −18 | −17.38 | 0.62 | −17.87 | 0.13 |
| −14 | −13.41 | 0.59 | −13.79 | 0.21 |
| −10 | −9.36 | 0.64 | −9.59 | 0.41 |
| −6 | −5.25 | 0.75 | −5.87 | 0.13 |
| −2 | −1.06 | 0.94 | −1.85 | 0.15 |
| 0 | 0.89 | 0.89 | 0.75 | 0.75 |
| 2 | 2.83 | 0.83 | 2.23 | 0.23 |
| 6 | 6.66 | 0.66 | 6.19 | 0.19 |
| 10 | 10.66 | 0.66 | 10.12 | 0.12 |
| 14 | 14.67 | 0.67 | 14.08 | 0.08 |
| 18 | 18.68 | 0.68 | 18.27 | 0.27 |
| | $\mu = 0.70$ | $\sigma = 0.11$ | $\mu = 0.19$ | $\sigma = 0.10$ |

The diagonal angles where both the PA and SA were rotated together were examined to determine if the ACE still was able to correctly track the pose. This time for this step, the angle set reverted back to original [±4°±8°±12°±16°±20°], but as pairs of both PA and SA. Table 3 shows the mean and standard deviation of the error for the PA and SA, in each respective quadrant. A test angle used was [+4,−4], that is, positive four degrees for PA and negative four degrees in SA.

TABLE 3

Experimental results for diagonal angles

Angle Difference Error

| | | +PA | | -PA | |
|---|---|---|---|---|---|
| -SA | PA | μ = 0.01 | σ = 0.13 | PA  μ = 0.02 | σ = 0.37 |
| | SA | μ = 0.26 | σ = 0.31 | SA  μ = 1.90 | σ = 0.34 |
| +SA | PA | μ = 0.41 | σ = 0.17 | PA  μ = 0.46 | σ = 0.06 |
| | SA | μ = 0.04 | σ = 0.17 | SA  μ = 1.25 | σ = 0.26 |

Discussion and Conclusion

Figure 6:
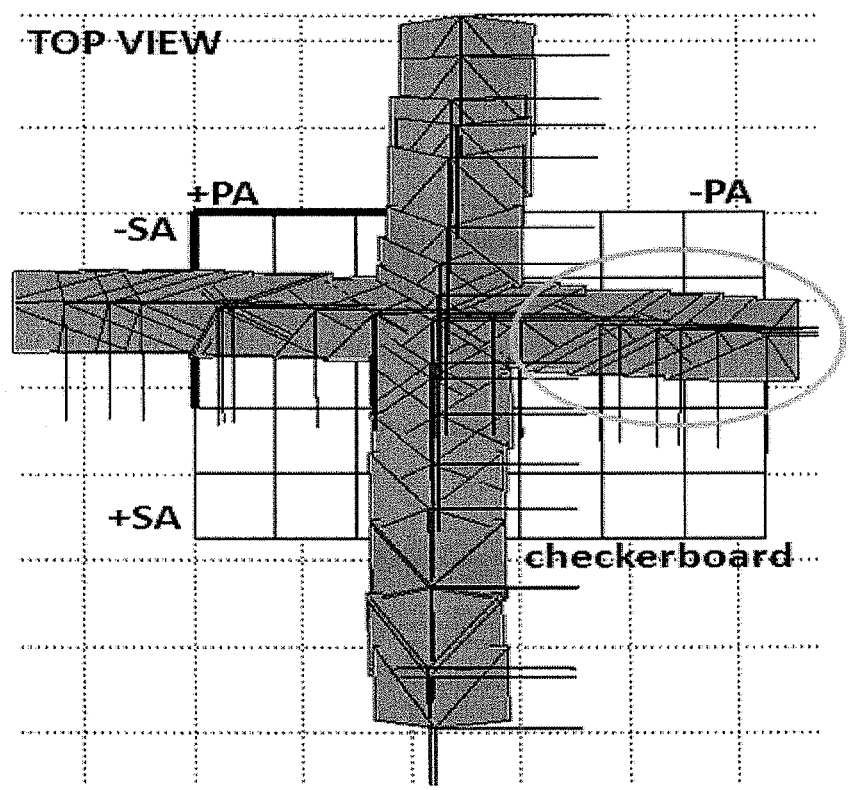
FIG. 6 is a plot showing the webcam's rotational path computed from the calibration images for the C-arm analogue of FIG. 3(a).

A linear relationship between the webcam C-arm angles and accelerometer angles was determined. According to Table 1 and FIG. 5(b), an offset equation that properly relates the accelerometer angles to the webcam angles was derived. Table 2 shows that by using ACE, the accelerometer can properly track the webcam pose with less than 1° of error. According to Table 3, the accelerometer can simultaneously track the PA and SA with a high degree of reliability. Although some accuracy was lost for SA during PA negative rotations, this may be an artifact of the experimental C-arm analogue. When looking at the distribution of the pose of calibration images, the C-arm rotations suggest a wobbling trajectory, as shown in FIG. 6. The circled areas highlight the most probable causes for the decreased accuracy, since the PA rotational path does not remain straight, slanting into the positive SA direction. This in turn affects the proper tracking of the SA by creating an unaccounted for offset.

Figure 7:
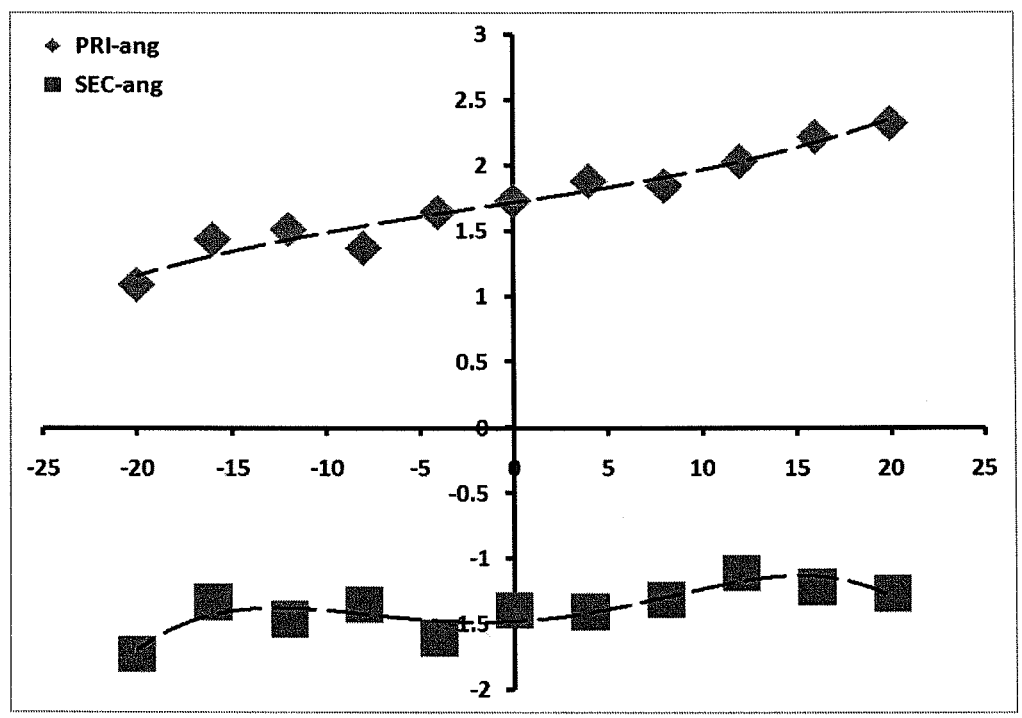
FIG. 7 is a plot showing a polynomial fit applied to the data of Table 1, for the C-arm analogue of FIG. 3(a).

It is also possible to apply a more complex polynomial fit to the webcam C-arm angle data and accelerometer angle data, such as shown in FIG. 7. For example, polynomial fit lines were used to create the ACE shown in Equations (5) and (6) below:

Let x represent initial PA then the new $$PA' = 2E^{-05} \cdot x^3 + 9E^{-05} \cdot x^2 + 1.022 \cdot x + 1.734 \quad (5)$$

Let z represent initial SA then the new $$SA' = -6E^{-06} \cdot z^4 + 6E^{-06} \cdot z^3 + 0.002 \cdot z^2 + 1.008 \cdot z + 1.478 \quad (6)$$

The data of Table 4 demonstrate the utility of using these equations, generated from polynomial fit lines, for webcam C-arm pose tracking.

TABLE 4

Polynomial ACE Pose Tracking

| | Primary Angle (PA) | | Secondary Angle (SA) | |
|---|---|---|---|---|
| Accelerometer Readings | Webcam Angles | Differences | Webcam Angles | Differences |
| -20 | -20.47 | -0.47 | -20.09 | -0.09 |
| -16 | -16.58 | -0.58 | -16.32 | -0.32 |
| -12 | -12.45 | -0.45 | -12.05 | -0.05 |
| -8 | -8.11 | -0.11 | -7.51 | 0.49 |
| -4 | -4.13 | -0.13 | -3.27 | 0.73 |
| 0 | 0.51 | 0.51 | 0.83 | 0.83 |
| 4 | 4.06 | 0.06 | 5.05 | 1.05 |
| 8 | 8.12 | 0.12 | 9.27 | 1.27 |
| 12 | 12.34 | 0.34 | 13.37 | 1.37 |
| 16 | 16.39 | 0.39 | 17.56 | 1.56 |
| 20 | 20.53 | 0.53 | 22.31 | 2.31 |
| | μ = 0.02 | σ = 0.40 | μ = 0.83 | σ = 0.79 |

Results showed that the third order polynomial for PA correction helped to improve the accuracy of pose tracking with slightly less precision. However, the forth order polynomial for SA correction was unsuccessful in tracking the pose. Thus, the results showed that in one case a better (polynomial) relationship was found, while in the other case the original (linear) relationship was better. Thus, one embodiment of the ACE creation step of the technique includes a testing loop wherein two or more fitting methods are examined, and the best fitting method is used for determining C-arm pose. However, the results show that a simple linear fit works well for such an application.

Similar results are expected when the method is applied to an actual C-arm device. Implementation on a C-arm using a webcam affixed to either the source or detector will allow examination of the characteristics of a full size C-arm, including deflection, bending and wheel motion of the C-arm, without exposure to harmful radiation. Deflections may arise from the heavy detector and source, where positions further from vertical will cause the C-arm structure to flex. Also, any wheels and wheel locks on the C-arm unit may give rise to subtle motion of the unit when rotating the C-arm. For example, mobile C-arms use wheel locks to secure the device in place, but during rotational movement the C-arm experiences rocking and swinging motions that affect the pose of the image. It remains to be seen whether the effect of any such motion amounts to significant pose error.

In conclusion, these results demonstrate an alternative tracking method that uses the tilt-sensing capabilities of accelerometers. By placing an accelerometer directly on the C-arm, the C-arm pose was determined from the accelerometer angle. The method requires a single calibration step that yields an offset for correction between accelerometer angles and C-arm angles.

EXAMPLE 2

The results of Example 1 suggested that deformation of the C-arm structure due to the force of gravity acting on the heavy X-ray source and detector may introduce an unaccounted for offset that would lead to inaccurate tracking of the C-arm pose. To investigate this a webcam was mounted on a full scale C-arm unit. The webcam allowed testing without exposure to ionizing radiation.

In an actual clinical application, the ground truth pose would be computed using a radio-opaque fluoroscope tracking fiducial such as the one developed by Jain et al [3]. In this example, optical imaging was applied with the webcam mounted externally on the gantry over the exit point of the X-ray source. The webcam tracked a checkerboard pattern that provided ground-truth C-arm poses of the 2D images through standard camera calibration techniques.

Angle Correction Equations

Figure 8:
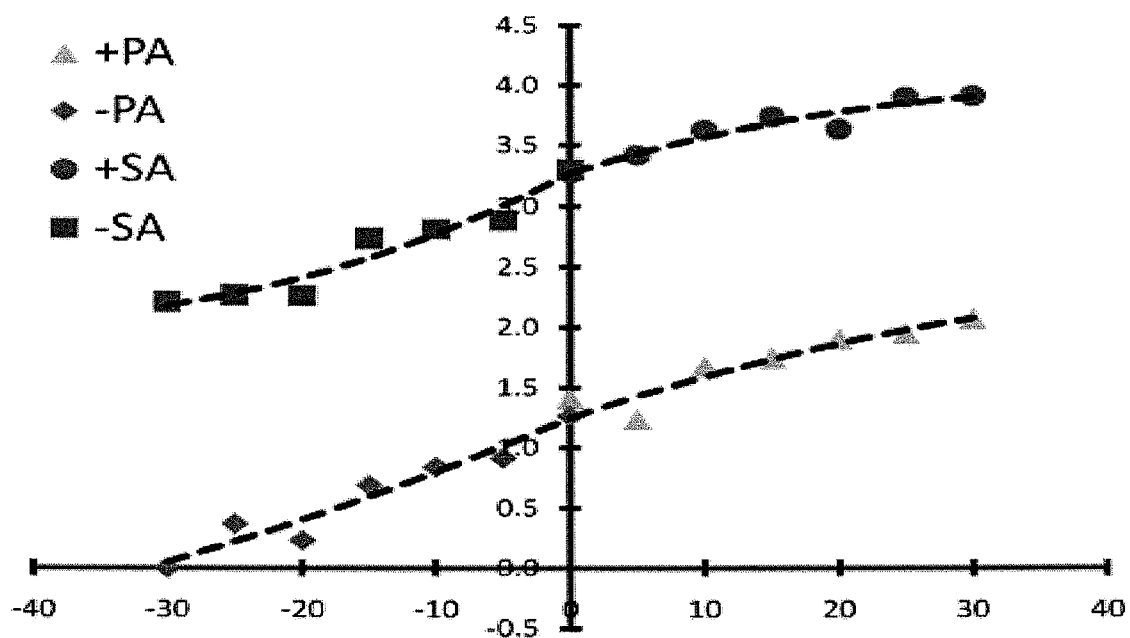
FIG. 8 is a plot of the differences and fitted lines used to generate angle correction equations for a C-arm fluoroscope.

To determine the initial offset a set of test images were taken, in step-and-shoot mode, at the angles [0°±5°±10°±15°±20°±25°±30°] using the initial accelerometer angle reading for the primary angle (PA) and secondary angle (SA) independently. These were chosen to give enough separation between angles with a wide range to account for changes in the C-arm motion, as well as encapsulating the clinical angle limitation motivating this work. It should be noted that acquiring more angles may improve modeling, but when used in actual X-ray imaging that would increase radiation exposure. However, optimization of the instant methods may reduce the angle set while achieving proper tracking. Next, the actual pose angles of the images were computed and the differences calculated. By graphically visualizing the differences (FIG. 8), best fit methods were applied, and the ACEs were generated (see Equations (7) and (8) below). Interestingly, the structure of the C-arm creates non-linear trends that required piecewise functions for modeling. The intercept values in the functions were set the same to avoid sudden shifts in the output during sign changes of the angles when the accelerometer is operating.

Let x represent the initial PA then the new output angle $$PA^* = \begin{cases} -0.0003 \cdot x^2 + 1.037 \cdot x + 1.250 & x \geq 0 \\ 0.0002 \cdot x^2 + 1.047 \cdot x + 1.250 & x < 0, \end{cases} \quad (7)$$

Let z represent the initial SA then the new output angle $$SA^* = \begin{cases} -0.0004 \cdot z^2 + 1.034 \cdot z + 3.270 & z \geq 0 \\ 0.0007 \cdot z^2 + 1.051 \cdot z + 3.270 & z < 0. \end{cases} \quad (8)$$

Structural Compensation Equations

An initial test of the ACEs (Equations (7) and (8)) showed that proper pose tracking of the C-arm was achieved, but only for independent angle rotations. The chart of FIG. 9 shows that PA and SA were accurately tracked independently, but less accurately simultaneously. It is believed that structural deformation of the C-arm is dependent on PA and SA and responsible for the loss of accuracy. As the rotation angle of the source or detector moves further from vertical, the effect of gravity becomes greater. This dependence on the pose angle of the C-arm required compensation for the structural deformation of the C-arm.

Figure 10A:
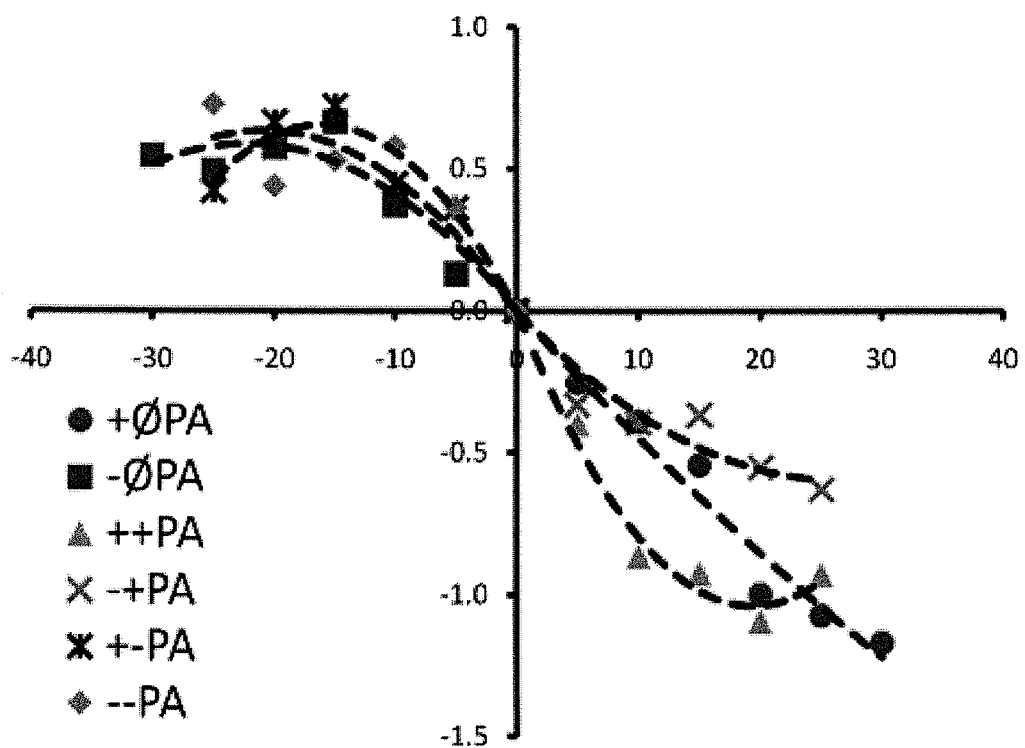
FIGS. 10(a) and 10(b) show C-arm deformations with accompanying best fit lines for PA (a) and SA (b), wherein the horizontal axis represents the rotational angle, and the vertical axis indicates the amount of deformation.
Figure 10B:
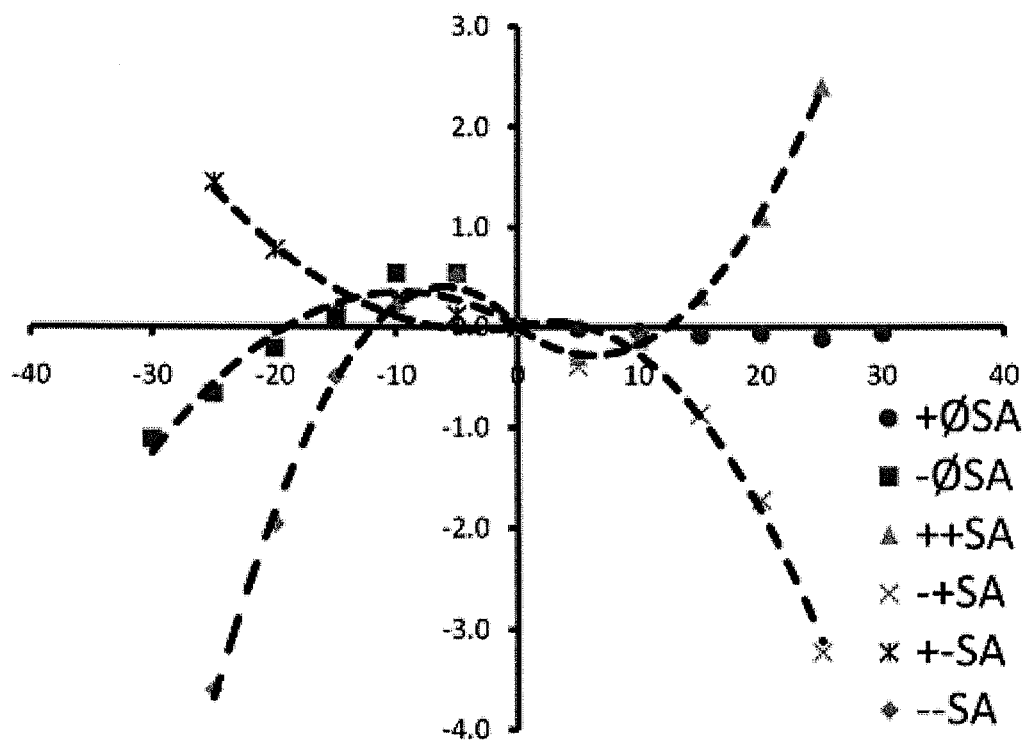

Structural compensation equations (SCEs) were formulated by reprocessing the test images that created the ACEs, with additional diagonal combinations of PA and SA, shown in the chart of FIG. 9. The errors were computed and zeroed to visualize the deformation for both the PA and SA separately. Line fitting was applied to the differences (FIG. 10). The plots show that a significant amount of deformation exists and zeroing the error creates a single starting position to make compensation easier to handle. A threshold value of r helped to control when to activate compensation depending on the current angle values for PA and SA. A series of equations was created as piecewise functions separated into ±PA and ±SA quadrants, shown below:

Let w=PA* and x=SA* then the compensated angle $$PA^\dagger = \begin{cases} w + (0.0002 \cdot x^2 - 0.047 \cdot x) & x \geq 0 \\ w + (-0.0012 \cdot x^2 - 0.053 \cdot x) & x < 0 \\ w + (0.0028 \cdot x^2 - 0.107 \cdot x) & w > \tau, x > \tau \\ w + (0.0008 \cdot x^2 - 0.045 \cdot x) & w < -\tau, x > \tau \\ w + (-0.0025 \cdot x^2 - 0.081 \cdot x) & w > \tau, x < -\tau \\ w + (-0.0015 \cdot x^2 - 0.061 \cdot x) & w < -\tau, x < -\tau, \end{cases} \quad (9)$$

$$SA^\dagger = \begin{cases} x & w \geq 0 \\ x + (-0.0038 \cdot w^2 - 0.073 \cdot w) & x < 0 \\ x + (0.0075 \cdot w^2 - 0.093 \cdot w) & w > \tau, x > \tau \\ x + (0.0030 \cdot x^2 - 0.019 \cdot w) & w < -\tau, x > \tau \\ x + (-0.0065 \cdot x^2 - 0.038 \cdot w) & w > \tau, x < -\tau \\ x + (-0.0113 \cdot w^2 - 0.135 \cdot w) & w < -\tau, x < -\tau. \end{cases} \quad (10)$$

Results and Discussion

Figures 12A, 12B:
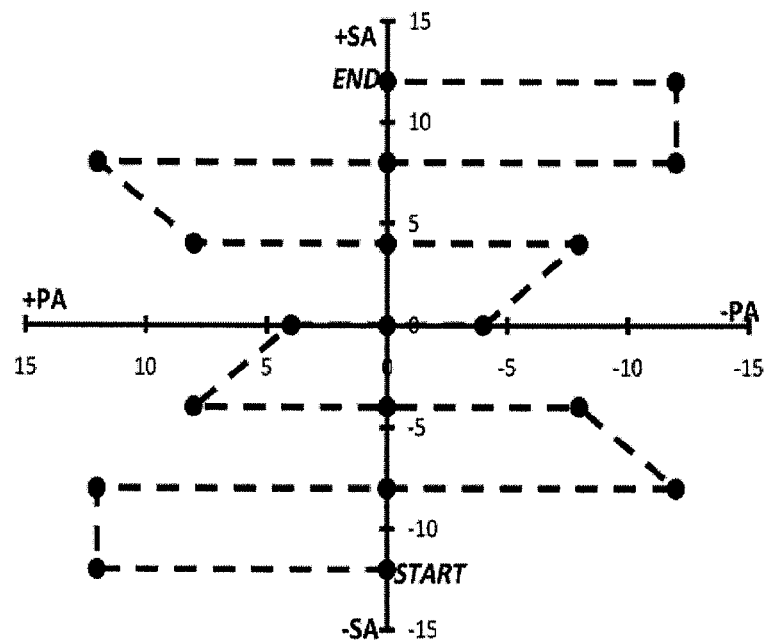
FIG. 12(a) is a plot of a sequential rotation path of the C-arm, where dots represent locations where images were acquired.
FIG. 12(b) is a chart showing the tracking results when the ACEs and SCEs were applied.

To characterize how accurately the ACEs and SCEs tracked the webcam C-arm pose a series of tests was performed. For the first test, the test image angles were changed for PA and SA to [0°±2°±6°±10°±14°±18°±22°±26°] for both independent and combinational rotation of PA and SA. This change was made to include different angles than those used to create the equations, so that they could be independently evaluated. The results, in chart form, are shown FIG. 11. The ACEs and SCEs tracked the C-arm pose with an average error of μ=0.11° and standard deviation of σ=0.21° for PA, and average error of μ=0.08° and standard deviation of σ=0.36° for SA. A second test was performed to investigate whether the C-arm pose could be tracked when subjected to sequential rotation path with results shown in FIGS. 12(*a*) and 12(*b*).

The results show that C-arm rotation encoding with an accuracy and precision of less than 0.5° was achieved using an accelerometer as tilt sensor. Use of the Structural Compensation Equations (SCEs) contributed to this result. These equations worked in tandem with the Angle Correction Equations (ACEs) to compensate for the inherent structural deformation of the C-arm experienced at different rotational poses. Excellent rotation encoding was achieved for the entire clinically relevant C-arm working range, at least in applications such as prostate brachytherapy.

For other clinical application areas where the working range may be larger, the method may be less accurate at larger combined rotational poses. This effect could be attributed to the threshold values used to set the point when the SCEs start compensating for structural deformation of the C-arm. The threshold values control activation of these equations, and the point at which they are activated may be adjusted. In this example, the SCEs were created by zeroing the offset, but this could also be carried out by monitoring for changes farther away from the origin. The reasoning behind this is that the lower angles about the vertical axis would have less deformation caused by gravity and could still be within the ACEs capability of tracking. Thus, determining a threshold location rather than a singular conditional value would provide an overall greater working range for tracking C-arm rotational poses as required in a broad range of applications.

Equivalents

Those skilled in the art will recognize or be able to ascertain variants of the embodiments described herein. Such variants are within the scope of the invention and are covered by the appended claims.

References

1. Barshan B, Durrant-Whyte HF (1995) Inertial navigation system for mobile robots. IEEE Trans Robotics Automation 11(2):328-245.
2. Batista J, Araujo H, Almeida A T (1996) Pose view stability analysis for camera look angles computation. In: Proceeding of the 13*th* International Conference on Pattern Recognition (ICPR), pp 171-175.
3. Jain A, Deguet A, Iordachita I, Chintalapani G, Blevins J, Le Y, Armour E, Burdette C, Song D, Fichtinger G (2007) Intra-operative 3D guidance in prostate brachytherapy using a non-isocentric C-arm. Medical Image Computing and Computer-Assisted Intervention 10(Pt 2):9-17.
4. Jain A, Fichtinger G (2006) C-arm tracking and reconstruction without an external tracker. Medical Image Computing and Computer-Assisted Intervention 9(Pt 1):494-502.
5. Jain A, Mustafa T, Zhou Y, Burdette C, Chirikjian G S, Fichtinger G (2006) FTRAC-A robust fluoroscope tracking fiducial. Medical Physics 32(10):3185-3198.
6. Lee J, Liu X, Jain A K, Song D Y, Burdette E C, Prince J L, Fichtinger G (2009) Prostate brachytherapy seed reconstruction with Gaussian blurring and optimal coverage cost. IEEE Transactions on Medical Imaging 28(12):1955-68.

7. Peters T, Cleary K (2008) In: (Eds.) Image-Guided Interventions: Technology and Applications, Springer.
8. Nikbakht S, Mazlom M, Khayatian A (2005) Evaluation of solid-state accelerometer for positioning of vehicle. IEEE International Conference on Industrial Technology (ICIT), pp 729-733.
9. Tan C W, Park S (2005) Design of accelerometer-based inertial navigation system. IEEE Transactions on Instrumentation and Measurement 54(6):2520-2530.
10. Thong Y K, Woolfson M S, Crowe J A, Hayes-Gill B R, Jones D A (2004) Numerical double integration of acceleration measurement in noise. Measurement 36:73-92.
11. Yao J, Taylor R H, Goldberg R P, Kumar R, Bzostek A, Van Vorhis R, Kazanzides P, Gueziec A (2000) A C-arm fluoroscopy-guided progressive cut refinement strategy using a surgical robot. Computer Aided Surgery 5(6):373-90.
12. Zhang N F (2006) Calculation of the uncertainty of the mean of autocorrelated measurements. Metrologia 43:S276-S281.
13. Gorges S, Kerrien E, Berger M-O, et al. (2005) Model of a Vascular C-Arm for 3D Augmented Fluoroscopy in Interventional Radiology, MICCAI 2005, Lecture Notes in Computer Science Vol. 3750, pp. 214-222, Springer.

The invention claimed is:

1. A method for estimating C-arm fluoroscope rotation pose, comprising:
    measuring at least one static gravitational angle of the C-arm using an accelerometer affixed to the C-arm, wherein the accelerometer is not moving during the measurement;
    determining, at least one difference between the at least one static gravitational angle of the C-arm and an image pose angle; and
    estimating C-arm fluoroscope rotation pose based on the at least one difference.

2. The method of claim 1, comprising:
    providing an object for determining ground truth of a fluoroscopy image space;
    acquiring a first set of fluoroscopy images at a plurality of C-arm poses and obtaining static gravitational angles for primary angles (PAs) and secondary angles (SAs) of each C-arm pose;
    calculating an actual C-arm pose for each image using the ground truth;
    determining differences between actual C-arm poses and corresponding static gravitational angles;
    generating angle correction equations by applying a best fit model to the differences; and
    using the angle correction equations to determine C-arm fluoroscopy rotation pose of subsequent C-arm fluoroscopy images.

3. The method of claim 2, further comprising generating structural compensation equations (SCEs) by:
    processing images with diagonal combinations of PA and SA;
    computing and zeroing errors for the PA and SA separately; and
    applying line fitting to differences between actual C-arm poses and corresponding static gravitational angles;
    wherein the method includes using angle correction equations and structural compensation equations to determine C-arm fluoroscopy rotation pose of subsequent C-arm fluoroscopy images.

4. The method of claim 3, comprising:
    determining a threshold value $\tau$; and
    using $\tau$ to control when to activate the structural compensation equations depending on angle values for PA and SA.

5. The method of claim 2, comprising using a fiducial to determine ground truth of the fluoroscopy image space.

6. The method of claim 2, comprising using a tracker to determine ground truth of the fluoroscopy image space.

7. The method of claim 2, wherein applying a best fit model to the differences comprises applying a linear regression model to the differences.

8. The method of claim 2, wherein applying a best fit model to the differences comprises applying a polynomial regression model to the differences.

9. The method of claim 2, including acquiring the first set of fluoroscopy images at a range of poses corresponding to a range of primary and secondary angles of the fluoroscope during use on a patient.

10. Programmed media for use with a computer and a fluoroscope including an accelerometer, the programmed media comprising:
    a non-transitory computer-readable medium encoded with a computer program, the computer program containing instructions to direct the computer to perform one or more of:
    input ground truth data of a fluoroscopy image space;
    acquire a first set of fluoroscopy images at a plurality of C-arm poses and obtain static gravitational angles for primary angles (PA) and secondary angles (SA) of each C-arm pose;
    calculate an actual C-arm pose for each image using the ground truth;
    determine differences between actual C-arm poses and corresponding static gravitational angles;
    generate angle correction equations by applying a best fit model to the differences;
    use the angle correction equations to determine C-arm fluoroscopy rotation pose of subsequent C-arm fluoroscopy images; and
    output rotation pose data of the subsequent C-arm fluoroscopy images.

11. The programmed media of claim 10, wherein the computer program directs the computer to:
    process images with diagonal combinations of PA and SA;
    compute and zero errors for the PA and SA separately; and
    apply line fitting to differences between actual C-arm poses and corresponding static gravitational angles to generate structural compensation equations; and
    use angle correction equations and structural compensation equations to determine C-arm fluoroscopy rotation pose of subsequent C-arm fluoroscopy images.

12. The programmed media of claim 11, wherein the computer program directs the computer to:
    determine a threshold value $\tau$; and
    use $\tau$ to control when to activate the structural compensation equations depending on angle values for PA and SA.

13. A kit, comprising:
    an accelerometer; and
    the programmed media of claim 10.

14. The kit of claim 13, further comprising hardware for interfacing the accelerometer with a C-arm fluoroscope and/or with a computer.

15. The kit of claim 13, comprising an object for determining ground truth of the fluoroscope.

16. The kit of claim 15, wherein the object for determining ground truth of the fluoroscope comprises a tracker or a fiducial.

* * * * *